(12) United States Patent
Fankhauser et al.

(10) Patent No.: US 9,060,866 B2
(45) Date of Patent: Jun. 23, 2015

(54) JOINT PROSTHESIS WITH INTERMEDIATE ELEMENT HAVING DIFFERENTLY FORMED SLIDING SURFACES

(75) Inventors: Christoph Fankhauser, Solothurn (CH); Walter Supper, Grenchen (CH); Daniel Delfosse, Jergenstorf (DE); Tobias Wyss, Kehrsatz (CH)

(73) Assignee: MATHYS AG BETTLACH, Bettlach (CH)

( * ) Notice: Subject to any disclaimer, the term of this patent is extended or adjusted under 35 U.S.C. 154(b) by 1345 days.

(21) Appl. No.: 11/885,497

(22) PCT Filed: Nov. 28, 2005

(86) PCT No.: PCT/EP2005/012700
§ 371 (c)(1),
(2), (4) Date: Jan. 3, 2008

(87) PCT Pub. No.: WO2006/092167
PCT Pub. Date: Sep. 8, 2006

(65) Prior Publication Data
US 2008/0161918 A1   Jul. 3, 2008

(30) Foreign Application Priority Data
Mar. 2, 2005   (DE) .................. 10 2005 009 496

(51) Int. Cl.
*A61F 2/38* (2006.01)
(52) U.S. Cl.
CPC . *A61F 2/38* (2013.01); *A61F 2/389* (2013.01); *A61F 2/3868* (2013.01)

(58) Field of Classification Search
CPC .......... A61F 2/38; A61F 2/389; A61F 2/3868
USPC ................. 623/20.33, 20.28, 20.32
See application file for complete search history.

(56) References Cited

U.S. PATENT DOCUMENTS

| 5,413,604 | A | 5/1995 | Hodge | |
| 5,871,543 | A | 2/1999 | Hofmann | |
| 5,879,392 | A * | 3/1999 | McMinn | 623/20.28 |
| 6,190,415 | B1 | 2/2001 | Cooke et al. | |
| 6,558,427 | B2 * | 5/2003 | Leclercq et al. | 623/20.33 |
| 7,066,963 | B2 * | 6/2006 | Naegerl | 623/20.32 |

(Continued)

FOREIGN PATENT DOCUMENTS

| DE | 3 444 001 | 6/1986 |
| DE | 1 95 29 824 | 2/1997 |

(Continued)

*Primary Examiner* — Bruce E Snow
*Assistant Examiner* — Melissa Hoban
(74) *Attorney, Agent, or Firm* — Scully, Scott, Murphy & Presser, P.C.

(57) ABSTRACT

A knee joint endoprosthesis (1) for forming an articulation between a femur and a tibia includes a femur component (2), which is connected to the femur, a tibia component (4), which is connected to the tibia, and an intermediate element (3) which is mounted between the tibia component (4) and the femur component (2). This intermediate element lies against the femur component (2) with a modular sliding surface (9) which includes a lateral sliding surface (9a) and a medial sliding surface (9b), and can be connected in a releasable manner to the tibia component (4). The lateral sliding surface (9a) and the medial sliding surface (9b) of the intermediate element (3) have different sagittal cross-sectional profiles.

7 Claims, 3 Drawing Sheets

(56) References Cited

U.S. PATENT DOCUMENTS

Figure 1A:
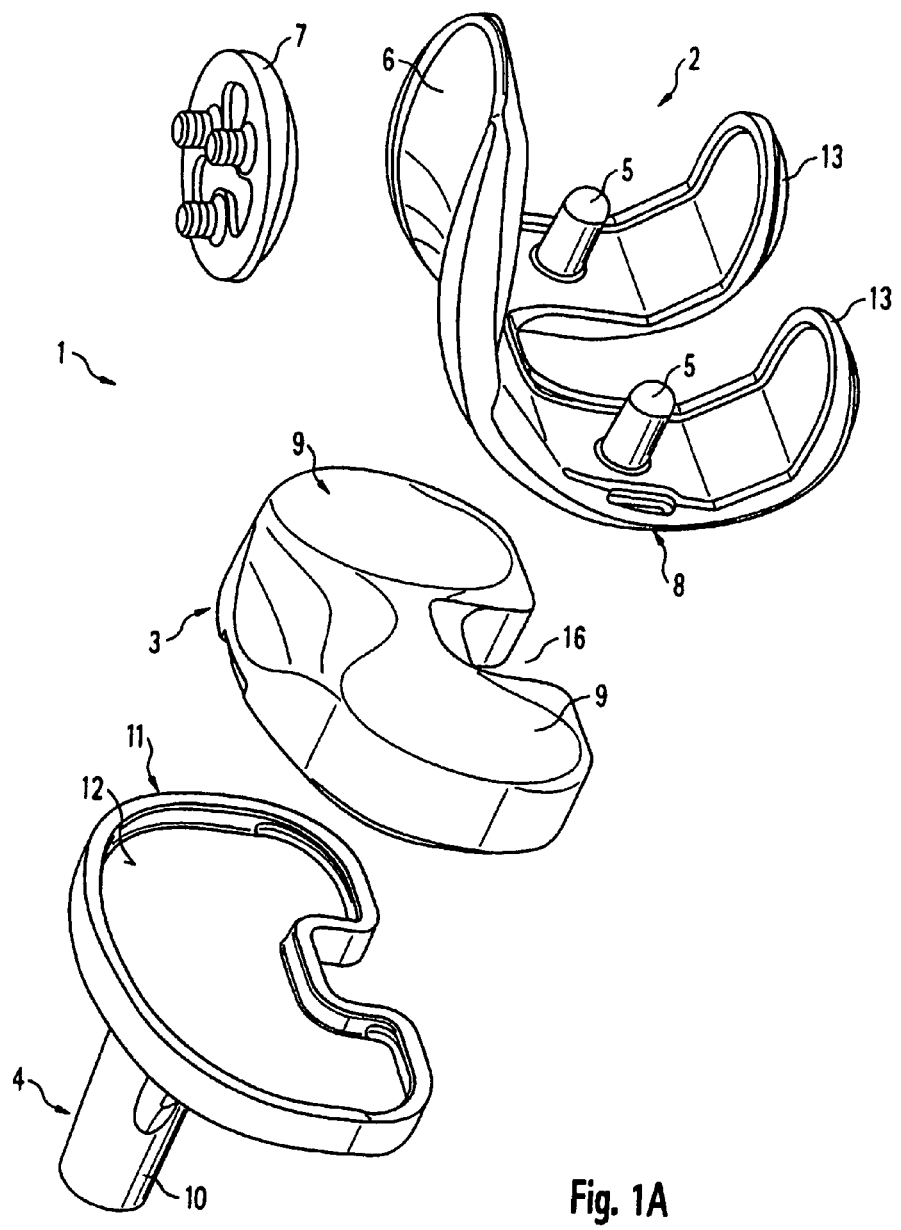

| | | | |
|---|---|---|---|
| 2003/0100953 A1* | 5/2003 | Rosa et al. | 623/20.3 |
| 2004/0006393 A1* | 1/2004 | Burkinshaw | 623/20.3 |
| 2004/0186582 A1* | 9/2004 | Yasuda et al. | 623/20.21 |
| 2005/0197710 A1* | 9/2005 | Naegerl | 623/20.32 |
| 2005/0209703 A1* | 9/2005 | Fell | 623/20.33 |

FOREIGN PATENT DOCUMENTS

| | | |
|---|---|---|
| EP | 0 765 645 | 4/1997 |
| WO | WO 98/02116 | 1/1998 |

* cited by examiner

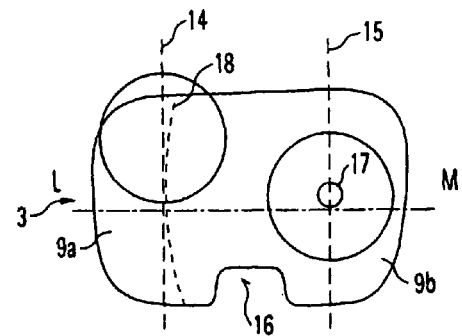
Fig. 1B
Prior art
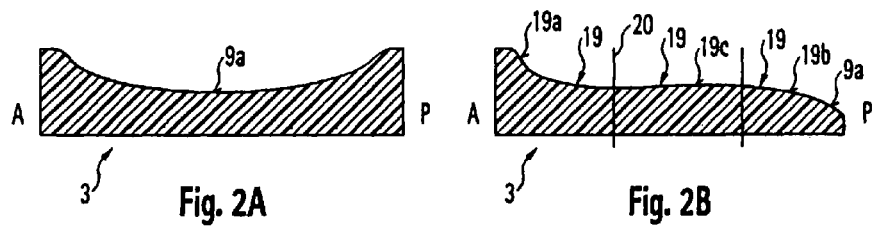
Fig. 2A
Fig. 2B
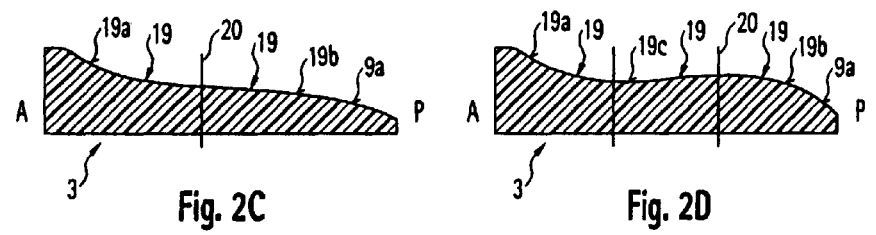
Fig. 2C
Fig. 2D
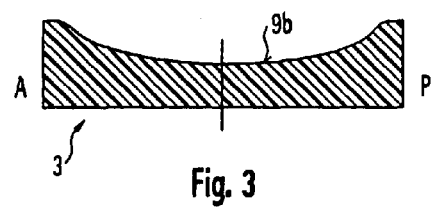
Fig. 3

JOINT PROSTHESIS WITH INTERMEDIATE ELEMENT HAVING DIFFERENTLY FORMED SLIDING SURFACES

The invention relates to a joint prosthesis for forming an articulation between a pair of human or animal bones.

A knee joint endoprosthesis which comprises a femur part and a tibia part is known from WO 98/02116, for example. In this case at least the surface of the medial condyle portion of the femur component is of approximately the same form as a medial cavity in the surface of the tibia component, so that all-over contact is obtained. Here the tibia component comprises a base part and a sliding component which is fixed on the latter in a releasable and displaceable manner.

A similar knee joint endoprosthesis is also known from EP 0 765 645 A2. In this case an improvement in the sequences of motions is to be obtained by enlarging the coronary radius of the sliding surface of the femur component in the anterior-posterior direction.

The disadvantage of the endoprostheses which are known from the above-mentioned publications lies in particular in the fact that, due to the unnatural knee joint shape of the sliding components, the physiological knee joint functions cannot be satisfactorily performed during motion and loading. Local load peaks occur in particular in consequence of line or point contact. Motor disturbances, uneven wear of the prosthesis, luxation or loosening of the tibial or femoral component of the endoprosthesis may occur as a result.

The object of the invention is accordingly to provide a joint prosthesis which, as far as possible, permits natural physiological sequences of motions without the possibility of incorrect positions or instability and subsequent malfunctioning or destruction of the prosthesis occurring.

The object is achieved by a joint prosthesis according to the characterising features of the main claim in conjunction with the features constituting the preamble.

The invention is based on the recognition that it is advantageous for a lateral sliding surface and a medial sliding surface of the intermediate element disposed between the femur component and the tibia component to have different sagittal cross-sectional profiles. This results in greater comfort through an improved range of motion and a distinctly smaller load on the soft tissue structures for the patient provided with the prosthesis.

Advantageous developments of the invention are possible through the measures which are indicated in the subclaims.

A particular advantage in this case lies in the fact that the medial sliding surface is always curved in a concave manner, while the lateral sliding surface is shaped so that it is at least partly, in particular in the dorsal compartment, convex or plane, although downward sloping in the dorsal-distal direction.

The lateral sliding surface is advantageously divided into zones which have different radii of curvature.

The radii of curvature of the individual zones advantageously pass continuously into the radii of curvature of the adjacent zones at turning points.

A further advantage lies in the fact that the intermediate element may be made of polymers, ceramic and/or metallic materials. The polyethylene UHMWPE is particularly preferred in this respect.

Figure 4A:
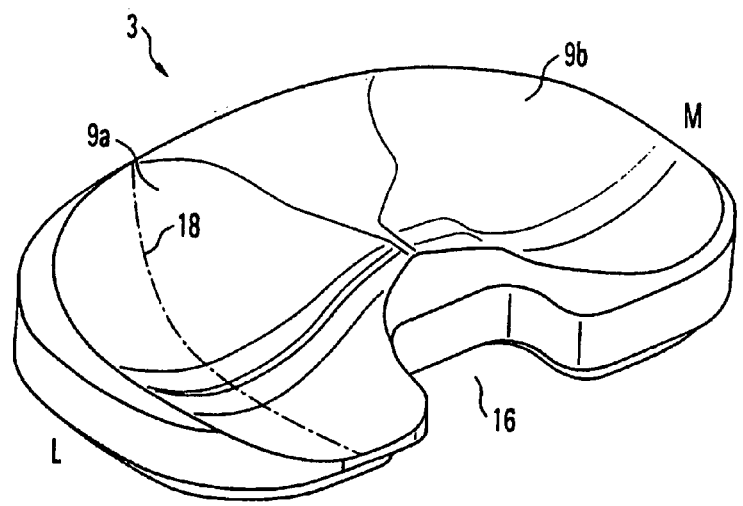
Figure 4B:
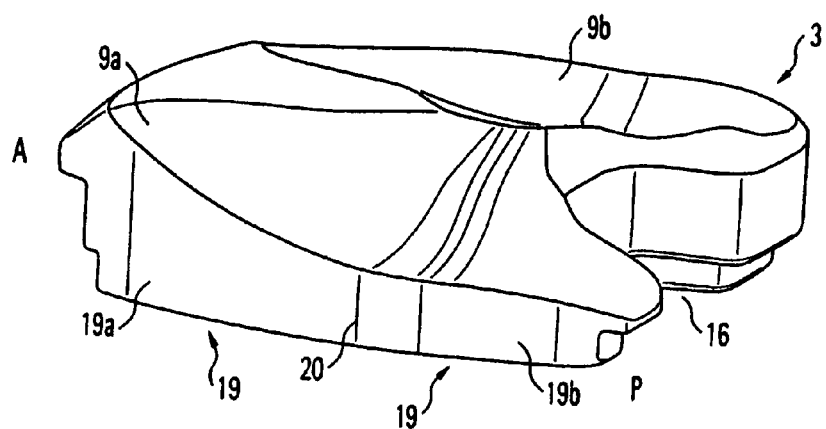

The invention is described in detail in the following on the basis of embodiments and with reference to the drawings, in which:

FIG. 1A shows an embodiment for a knee joint endoprosthesis according to the prior art, FIG. 1B shows an embodiment of an intermediate element of a knee joint endoprosthesis of a schematic plan view, FIGS. 2A-2D show embodiments for anterior-posterior cross-sectional shapes in a lateral sectional plane, FIG. 3 shows an embodiment of the anterior-posterior cross-sectional shape in a medial sectional plane, and FIGS. 4A-B are a schematic perspective and a schematic perspective, part-sectional view of the intermediate element according to FIG. 1B which is configured according to the invention.

Before representing embodiments of an intermediate element of a knee joint endoprosthesis according to the invention on the basis of FIGS. 2A to 2D, FIG. 3 and FIGS. 4A and 4B, a knee joint endoprosthesis according to the prior art shall firstly be illustrated in brief in terms of its essential components on the basis of FIG. 1A in order to provide a better understanding of the measures according to the invention.

The knee joint endoprosthesis 1 according to the prior art comprises a femur component 2 which is configured for the prosthetic provision of both condyles of the thighbone (femur). It is anchored in the thighbone by means of two pegs 5 and comprises an anterior sliding surface 6 for a patella implant 7 as well as distal sliding surfaces 8 which slide on an intermediate element 3.

The intermediate element 3 replaces the function of the menisci of the knee joint and also comprises sliding surfaces 9 which correspond with the distal sliding surfaces 8 of the femur component 2.

The intermediate element 3 is connected in a releasable manner to a tibia component 4 which is implanted with a shank 10 in a shinbone and serves as a support for the intermediate element 3. A recess 16 of the intermediate element 3 engages under a rim 11 with which the tibia component 4 is provided and which prevents the intermediate element 3 from travelling out of the knee joint gap. A contact surface 12 of the tibia component 4 may be plane, which simplifies production.

Following the preparatory resectioning of the femur and the tibia, the femur component 2 and the tibia component 4 are firstly inserted, after which an intermediate element 3, adapted to the situation, is placed in the tibia component 4.

As can be seen from FIG. 1A, the aim in this case is the prosthetic provision of both femur condyles through the represented bicondylar knee joint endoprosthesis 1. The intermediate element 3 consequently comprises the above-mentioned sliding surfaces 9, which are of a concave formation in the intermediate element 3, for the two condyle extensions 13 of the femur component 2.

However a formation of this kind of the intermediate element 3 can only reproduce the sequences of motions in the joint in a highly inadequate manner. The so-called range of motion is in particular highly limited in comparison with a natural knee joint. There are limitations to deep bending of the knee and the necessary axial internal rotation of the shinbone with increasing bending as a result of partial overstressing of ligamentary structures, which may subject the intermediate element 3 to undesirable and excessive stress and thereby increased wear.

In contrast to this, the intermediate element 3 of the knee joint endoprosthesis 1 according to FIG. 1B which is configured according to the invention has geometries of the sliding surfaces 9 which differ from the above.

FIG. 1B represents a schematic plan view onto an intermediate element 3 in which two sagittal sectional planes 14 and 15 are marked. Here the sectional plane 14 is provided laterally and the sectional plane 15 medially relative to the positioning of the intermediate element 3 in the joint.

According to the invention, the medial sagittal section in each case has an identical, concave shape according to FIG. 3, while the lateral sagittal sections according to FIGS. 2A to 2D may be selected so as to differ from this. In this respect the cross-sectional shape which is indicated in FIG. 2A denotes the prior art, as here a sliding surface 9 is produced which is concave both medially and laterally (FIG. 2A in conjunction with FIG. 3).

If, however, the medial concave cross-sectional shape according to FIG. 3 is combined with a cross-sectional shape according to FIGS. 2B to 2D, the result in each case is an intermediate element 3 which, due to the use of convex or at least plane radii of curvature, permits completely different sequences of motions which physiologically come far closer to the natural knee joint articulation.

A knee joint endoprosthesis which is thus configured can then be combined with a conventional femur component 2 which articulates on the sliding surface 9. The knee joint endoprosthesis 1 is then highly stable in extension and, with increasing flexion, can rotate medially about a point 17, which can only be slightly displaced in the anterior-posterior direction, on the medial tibial sliding surface 9b, and is marked on the sectional plane 15 in FIG. 1B, while the tibial internal rotation commences unimpeded. The femur component 2 can be displaced with increasing flexion in the posterior direction on the lateral tibial sliding surface 9a along the curved line which is marked by 18 in FIG. 1B and at the same time descend in the dorsal-distal direction, which permits unimpeded internal rotation of the shinbone, combined with a synchronous external rotation of the femur, and thus subjects individual soft tissues to less stress in accordance with normal kinematics in deep flexion and permits a greater range of motion.

The lateral sliding surface 9a of the intermediate element 3 is configured such that the centre of rotation of the lateral curved concave-flat-convex sliding surface 9a lies in the medial sliding surface 9b in the region 17. In the lateral sliding surface 9a there is a change in the dorsal radius of curvature as well as the height of the bearing surface as a function of the flexion of the knee and the internal rotation of the tibia.

Corresponding sectional profiles are represented in FIGS. 2B to 2D. Here the embodiments according to FIGS. 2B and 2D in each case comprise three zones 19 with different radii of curvature, while the embodiment according to FIG. 2C comprises two zones 19 with different radii of curvature. The radii of curvature in each case decrease from the anterior to the posterior, with the anterior and the posterior being marked by A and P in FIGS. 2 and 3.

Here the perpendicular lines in FIGS. 2B to 2D denote turning points 20 at which the radius of curvature of one zone 19 changes into the radius of curvature of an adjacent zone 19. The behaviour of the radii of curvature is in this respect constant. Consequently two turning points 20 of the radius of curvature can be seen in FIGS. 2B and 2D and one turning point 20 of the radius of curvature in FIG. 2C.

In extension the medial sliding surface 9b and the lateral sliding surface 9a are to a large degree congruent with the femur component 2, laterally in particular in the anterior region. The lateral sliding surface 9a, which is flat and/or slopes downwards in a convex manner, is configured such that the internal rotation of the tibia about the medial centre 17 takes place in the medial sliding surface 9b, while the so-called "rollback" of the femur in the dorsal/distal direction predominantly takes place on the lateral sliding surface 9a, with a rotation about the medial centre 17 taking place.

The aim is therefore to obtain a sliding surface 9 which comprises a concave medial sliding surface 9b and a lateral sliding surface 9a which slopes downwards in a ventrally concave, dorsally convex manner.

In extension the concave medial sliding surface 9b is to a large degree congruent with the femur component 2. The translatory degree of freedom of the femur component 2 in the anterior direction is controlled and limited by the sliding surface 9b, elevated at the posterior as well as the reaction force of the engaging soft tissue structures, so that sliding of the femur component 2 in the anterior direction is controlled and limited. Conversely, the translatory degree of freedom of the femur component 2 in the posterior direction is limited by the sliding surface 9b, elevated at the anterior, as well as the reaction force of the engaging soft tissue structures, and sliding of the femur component 2 in the posterior direction is thereby also limited, as is evident from FIG. 3.

In flexion the concave medial sliding surface 9b is also to a large degree congruent with the femur component 2, although not to such a great extent as in extension, which permits the external femur rotation as well as the movement of the femur component 2 on the lateral sliding surface 9a in the dorsal-distal direction about the point of rotation 17, which is located in the medial sliding surface 9b and is only displaced slightly in the anterior-posterior direction, for example only by 0-3 mm.

In contrast, the lateral sliding surface 9a is of concave-flat-convex formation. In extension the translatory degree of freedom of the femur component 2 in the anterior direction is limited by the sliding surface 9b, elevated at the anterior, as well as the reaction force of the engaging soft tissue structures, and sliding of the femur component 2 in the anterior direction is thereby controlled and limited. Although the translatory degree of freedom of the femur component 2 in the posterior direction is permitted through the convex shape of the sliding surface 9a, this movement is controlled and limited by the rotational movement of the femur which occurs about the medial point of rotation 17 and the femoral ligamentous apparatus which is thereby stretched, assisted by the high degree of congruency in the medial sliding surface 9b. The medial sliding surface 9b is therefore mainly responsible for stability, while the lateral sliding surface 9a is responsible for mobility and guidance.

In flexion the lateral sliding surface 9a is characterised by a convex, flat and/or concave sliding surface 9a which in the embodiment slopes downwards in the dorsal and distal direction and permits and assists the physiological femoral external rotation and accordingly the tibial internal rotation, which conforms with more physiological kinematics. In the dorsal-distal direction the dorsal tibial slope increases due to the convex form and the height therefore decreases. The point of contact between the femur component 2 and the intermediate element 3 is therefore displaced in the distal direction with increasing femoral "rollback".

Both sliding surfaces 9a and 9b of the modular sliding surface 9 have a concave shape in a frontal section, indicated in FIG. 1B by a dot-dash line, through the sliding surface 9a, 9b.

In order to illustrate the circumstances, FIGS. 4A and 4B present a schematic, perspective representation and a perspective, part-sectional view, respectively, of an intermediate element according to FIG. 1B which is configured according to the invention. The broken line 18 in FIG. 4A corresponds to the curved line 18 in FIG. 1B. The part-sectional view according to FIG. 4B shows a sectional area through the lateral sliding surface 9a along the line 18 which has a curved profile according to FIG. 2C which is configured according to the invention. The zones 19, 19*a*, 19*b* and the turning point 20, of which there is one in the embodiment, can clearly be seen.

The intermediate element 3 may be made of polymers, ceramic and/or metallic materials. The polyethylene UHMWPE is particularly preferred in this respect.

Advantages of the knee joint endoprosthesis configured according to the invention with an intermediate element 3 formed according to the above statements lie in particular in a greater range of motion of the knee, a reduction of the risk of impingement between the femur component 2 and the tibia component 4, the more physiological kinematics through less limited internal rotation of the tibia and external rotation of the femur, assisted by lowering the lateral sliding surface 9*a* in the dorsal-distal direction in deep flexion, long-term results thereby improved and, through soft tissue structures being stressed in a more physiological manner, the prevention of overloading of the latter, which can consequently reduce chronic pain.

The invention is not limited to the represented embodiments, but can rather be applied for a great many additional configuration possibilities of knee joint endoprostheses 1, in particular to cruciate ligament-preserving and cruciate ligament-sacrificing as well as coupled total knee joint prostheses 1 with a femur component 2 and a tibia component 4. All the features of the invention can in this respect be combined as desired.

The invention claimed is:

1. A knee joint endoprosthesis for forming an articulation between a femur and a tibia, comprising:
    a femur component which is connectable to the femur,
    a tibia component which is connectable to the tibia, and
    an intermediate element, which is mountable between the tibia component and the femur component and connectable in a releasable manner to the tibia component and which lies against the femur component with a modular sliding surface comprising a lateral sliding surface and a medial sliding surface,
    wherein:
    the lateral sliding surface and the medial sliding surface of the intermediate element have different sagittal cross-sectional profiles,
    the medial sliding surface, in the sagittal cross-section thereof, is curved in a concave manner,
    the lateral sliding surface, in the sagittal cross-section thereof, is curved ventrally in a concave manner and downwardly slopes dorsally in a convex manner,
    when the medial sliding surface is being used in extension and flexion:
    a translatory degree of freedom of the femur component in the anterior direction is controlled and limited by the medial sliding surface being elevated at the anterior, so that sliding of the femur component in the anterior direction is controlled and limited, and
    a translatory degree of freedom of the femur component in the posterior direction is limited by the medial sliding surface being elevated at the posterior, so that sliding of the femur component in the posterior direction is also limited, and
    when the lateral sliding surface is being used in extension and flexion:
    a translatory degree of freedom of the femur component in the anterior direction is limited by the lateral sliding surface being elevated at the anterior, so that sliding of the femur component in the anterior direction is controlled and limited, and
    a translatory degree of freedom of the femur component in the posterior direction is permitted through the convex shape of the downwardly sloping lateral sliding surface without any elevation, so that the movement of the femur component is controlled and limited by the rotational movement of the femur which occurs about a femoral ligamentous apparatus.

2. The knee joint endoprosthesis according to claim 1, wherein the sagittal cross-sectional profile of the medial sliding surface is at least partially concavely shaped.

3. The knee joint endoprosthesis according to claim 1, wherein a turning point is provided between the anterior zone and the at least one central zone and between the at least one central zone and the posterior zone.

4. The knee joint endoprosthesis according to claim 3, wherein the radii of curvature of the three zones pass continuously into one another at turning points lying between said zones, when said at least one central zone has a concave radius of curvature.

5. The knee joint endoprosthesis according to claim 1, wherein the intermediate element is made of a material selected from the group of materials consisting of a polymer or, a ceramic or a metallic material or composite metallic materials.

6. The knee joint endoprosthesis according to claim 5, wherein the polymer is polyethylene.

7. The knee joint endoprosthesis according to claim 6, wherein said polyethylene consists of UHMWPE (ultra high molecular weight polyethylene).

* * * * *